July 4, 1972 R. KORDES Plant Pat. 3,228
ROSE PLANT
Filed Dec. 28, 1970
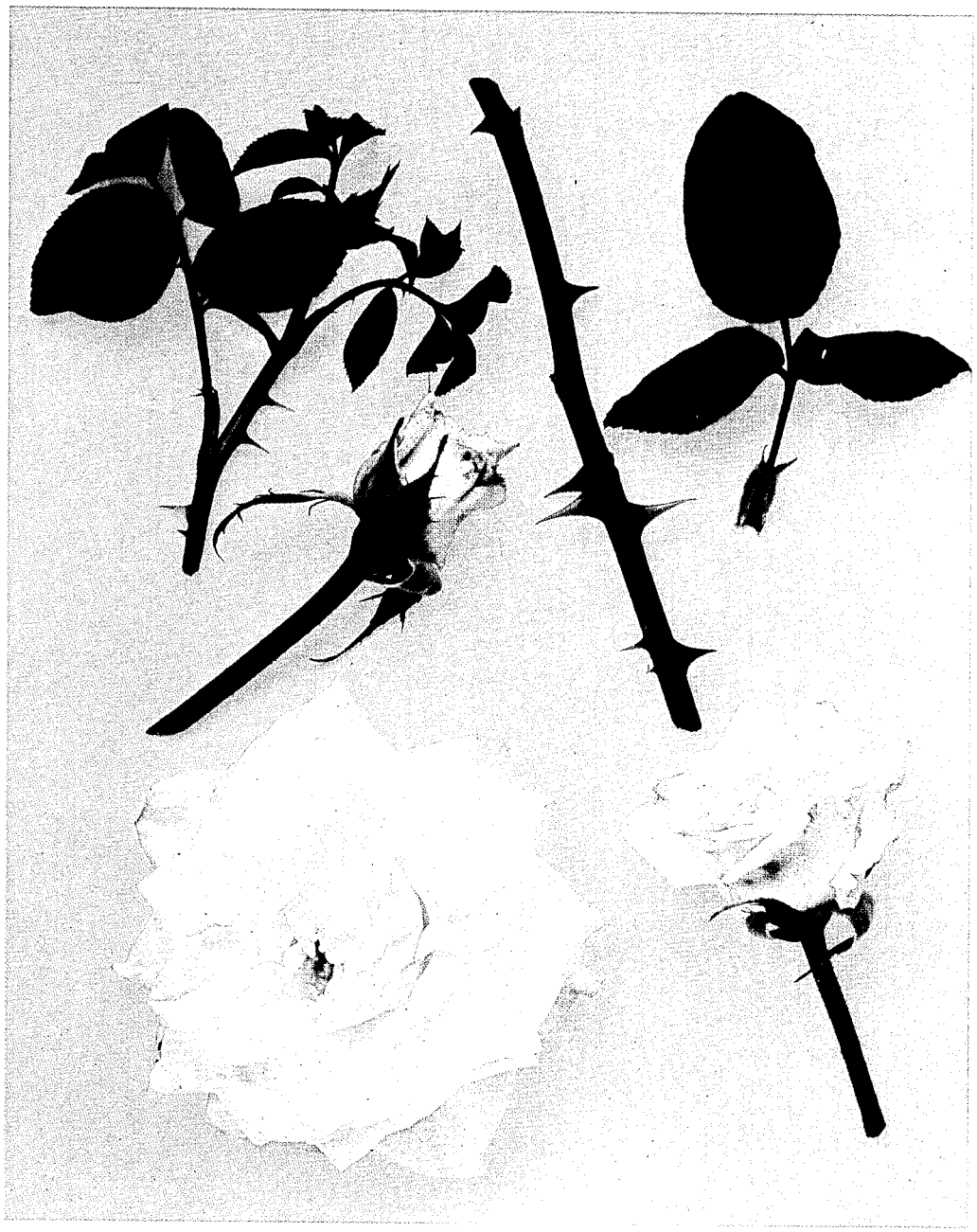
Inventor.
Reimer Kordes
By: Robbs & Robb
Attorneys.

United States Patent Office

Plant Pat. 3,228
Patented July 4, 1972

3,228
ROSE PLANT

Reimer Kordes, Holstein, Germany, assignor to Jackson & Perkins Company, Medford, Oreg.

Filed Dec. 28, 1970, Ser. No. 100,244
Int. Cl. A01h 5/00
U.S. Cl. Plt.—15 1 Claim The present invention relates to a new and distinct variety of rose plant of the hybrid tea class, which was originated by me by crossing the rose variety known as "Arlene Francis" (U.S. Plant Pat. No. 1,684) with the rose variety known as "Roselandia" (unpatented), the former being the seed parent and the latter being the pollen parent.

The primary objective of this breeding was to produce a new and improved rose variety of the hybrid tea class, which freely bears clear, light yellow flowers on a plant suitable for use both outdoors and for greenhouse-grown cut flowers. This objective was fully achieved, along with other desirable improvements, as evidenced by the following unique combination of characteristics which are outstanding in the new variety and which distinguish it from its parents, as well as from all other rose varieties of which I am aware:

(1) An unusually freely branched plant habit;
(2) Oval pointed and leathery leaflets of medium size and dark green color;
(3) A constant and unusually abundant blooming habit, so that the plants nearly always have flowers during the growing season;
(4) A uniform Mimosa Yellow flower color; and
(5) A moderately strong tea flower fragrance.

Asexual reproduction of my new variety by budding, as performed by me at Elmshorn, Holstein, Germany, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new rose variety, with color terminology in accordance with Wilson's Horticultural Colour Chart, except where general color terms of ordinary dictionary significance are obvious:

Parentage: Seedling.
*Seed parent.*—"Arlene Francis."
*Pollen parent.*—"Roselandia."
Classification:
*Botanic.*—*Rosa hybrid.*
*Commercial.*—Hybrid tea.
Propagation: Holds its distinguishing characteristics through succeeding propagations by budding.

*Flower*

(Observations made from specimens grown at Irvine, Calif., U.S.A., in afternoon during early November.)
Blooming habit: Recurrent—continuous.
Bud:
*Size.*—Medium; from 1¼ inches to 1½ inches long.
*Form.*—Long; flat top; broad base.
*Color.*—When sepals first divide—slightly darker than Dresden Yellow, Plate 64. When half-blown—inside of petals—Aureolin, Plate 3; reverse of petals—Lemon Yellow, Plate 4/1.
*Sepals.*—3 sepals lightly appendaged and 2 unappendaged sepals with smooth edge. Color—outside—Lettuce Green, Plate 861/2; inside—Lavender Green, Plate 000761, with tomentose surface.

*Receptacle.*—Color—Lettuce Green, Plate 861/2. Shape—funnel. Size—large; broad. Surface—smooth.
*Peduncle.*—Length—short. Surface—slightly prickly. Color—Spinach Green, Plate 0960/3, with reddish overlay on exposed side. Strength—stiff; erect.
*Opening.*—Spiral; petals curl back.
Bloom:
*Size.*—Large; from 4½ inches to 5 inches in diameter.
*Borne.*—Singly.
*Stems.*—Medium length.
*Form.*—High-centered. Permanence—retains its form to the end.
*Petalage.*—Number of petals under normal conditions—from 28 to 35.
*Color.*—Center of flower—upper side of petals—Mimosa Yellow, Plate 602/1; reverse side of petals—Mimosa Yellow, Plate 602/1. Outer petals—same as center petals. Base of petals—Mimosa Yellow, Plate 602/1.
*General tonality from a distance.*—Mimosa Yellow, Plate 602/1.
*Variegations.*—None.
*Discoloration.*—General tonality at end of first day—Mimosa Yellow, Plate 602/1. Third day—slightly lighter (Mimosa Yellow, Plate 602/2).
*Fragrance.*—Moderate. Nature—Tea.
Petals:
*Texture.*—Thin; leathery.
*Surface.*—Inside—satiny. Reverse—satiny.
*Shape.*—Round.
*Form.*—Edges slightly undulated.
*Arrangement.*—Imbricated.
*Petaloids in center.*—Few.
*Persistence.*—Drop off clearly.
*Lasting quality.*—On the plant—very long. As cut flower—long.

*Reproductive organs*

Anthers: Small; many; regularly arranged around styles. Color—Yellow.
Filaments (threads): Medium length. Color—Yellow.
Pollen: Color—Gold-yellow.
Styles: Loosely separated; uneven length.
Stigmas: Color—White.
Ovaries: All enclosed in calyx.
Fruit: None observed.

*Plant*

Form: Bush.
Growth: Very vigorous.
Foliage: Compound of 5 leaflets on normal mid-stem leaves.
*Size.*—Medium.
*Quantity.*—Normal.
*Color.*—New foliage—Near Oxblood Red, Plate 00823, overlaid with green. Old foliage—upper side—Parsley Green, Plate 00962. Under side—Spinach Green, Plate 0960/3.
*Leaflets.*—Shape—oval pointed. Texture—upper side—leathery; under side—smooth. Ribs and veins—impressed. Edge—serrated. Serration—single; small. Petiole (rachis)—color—Green; under side—prickly. Stipules—short; smooth.
*Disease resistance.*—Resistant to mildew and blackspot, as determined by comparison with other rose varieties grown under the same normal conditions at Irvine, Orange County, Calif., U.S.A.
Wood:
*New wood.*—Color—Spinach Green, Plate 0960/1. Bark—smooth.

*Old wood.*—Color—Spinach Green, Plate 0960. Bark—smooth.

Thorns:

*Thorns*—Quantity—on main stalks from base—ordinary; on laterals from stalk—ordinary. Form—Narrow base; long; straight. Color (when young)—Reddish-brown at base and on upper side; lighter on lower side. Position—irregular.

*Prickles.*—Quantity—on main stalks—few. On laterals—few. Color—Brown.

*Short needles.*—Quantity—on main stalks—none; on laterals—none.

I claim:

1. A new and distinct variety of rose plant of the hybrid tea class, substantially as herein shown and described, characterized particularly as to novelty by the unique combination of an unusually freely branched plant habit, oval pointed and leathery leaflets of medium size and dark green color, a constant and unusually abundant blooming habit, so that the plants nearly always have flowers during the growing season, a uniform Mimosa Yellow flower color, and a moderately strong tea flower fragrance.

No references cited.

ROBERT E. BAGWILL, Primary Examiner